United States Patent
Garcia-Rodenas et al.

(10) Patent No.: US 12,059,015 B2
(45) Date of Patent: Aug. 13, 2024

(54) MATERNAL SUPPLEMENT

(71) Applicant: SOCIETE DES PRODUITS NESTLE S.A., Vevey (CH)

(72) Inventors: Clara Lucia Garcia-Rodenas, Forel (CH); Michael Affolter, Savigny (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 18/203,306

(22) Filed: May 30, 2023

(65) Prior Publication Data

US 2023/0413886 A1 Dec. 28, 2023

Related U.S. Application Data

(63) Continuation of application No. 16/768,829, filed as application No. PCT/EP2018/082923 on Nov. 29, 2018, now Pat. No. 11,696,595.

(30) Foreign Application Priority Data

Dec. 1, 2017 (EP) ..................................... 17205002

(51) Int. Cl.
*A61K 31/00* (2006.01)
*A23L 33/155* (2016.01)
*A61K 31/07* (2006.01)
*A61K 31/355* (2006.01)
*A61K 31/455* (2006.01)
*A61K 33/04* (2006.01)
*A61K 33/30* (2006.01)

(52) U.S. Cl.
CPC ............ *A23L 33/155* (2016.08); *A61K 31/07* (2013.01); *A61K 31/355* (2013.01); *A61K 31/455* (2013.01); *A61K 33/04* (2013.01); *A61K 33/30* (2013.01)

(58) Field of Classification Search
CPC .................................. A61K 31/00; A61K 33/00
See application file for complete search history.

(56) References Cited

U.S. PATENT DOCUMENTS

2010/0119617 A1* 5/2010 O'Connor ............... A23C 3/08
424/602

FOREIGN PATENT DOCUMENTS

| CN | 1353577 A | 6/2002 |
|---|---|---|
| CN | 105722515 A | 6/2016 |
| WO | 0152835 | 7/2001 |
| WO | 2015161153 | 10/2015 |
| WO | 2016066460 | 5/2016 |
| WO | 2017037105 | 3/2017 |
| WO | 2017167419 | 10/2017 |

OTHER PUBLICATIONS

Moran et al. "Concentrations and Total Daily Output of Micronutrients in Breast Milk of Mothers Delivering Preterm: A Longitudinal Study" Journal of Pediatric Gastroenteroloty and Nutrition, 1983, vol. 2, pp. 629-634.
Bauer et al. "Longitudinal analysis of macronutrients and minerals in human milk produced by mothers of preterm infants" Clinical Nutrition, 2010, vol. 30, No. 2, pp. 215-220.
Lima Mayara Santa Rosa et al. "Breast milk retinol concentration in mothers of preterm newborns" Early Human Development, 2017, vol. 106, pp. 41-45.
English machine translation of Yang et al., CN 107242576 A, Oct. 2017, 2017.
Alam et al., "Effect of Dietary Fat Supplementation During Late Pregnancy and First Six Months of Lactation on Maternal and Infant Vitamin A Status in Rural Bangladesh", Journal of Health, Population, and Nutrition, vol. 28, Issue No. 4, 2010, pp. 333-342, XP009540958.
European Office Action for Appl No. 18 808 361.2-1112 dated Dec. 2, 2022.
Scholl et al., "Low zinc intake during pregnancy: its association with preterm and very preterm delivery," American Journal of Epidemiology 137(10):1115-1124, 1993.
Moran et al., "The relationship between zinc intake and serum/plasma zinc concentration in pregnant and lactating women: a systematic review with dose-response meta-analyses," Journal of Trace Elements in Medicine and Biology 26:7 4-79, 2012.
Butte et al. "Longitudinal ctianges in milk compositions of mottiers delivering preterm and term infants" Early Human Development, 1984, vol. 9, No. 2, pp. 153-162.
Dall'Agnola et al. "Post-disctiarge supplementation of vitamins and minerals for preterm neonates" Early Human Development, 2009, vol. 85, No. 10, pp. S27-S29.
Murphy et al. "Zinc deficiency a problem with preterm breast milk" Early Human Development, 1985, vol. 10, No. 3-4, pp. 303-307.
Mathur et al. "Zinc supplementation in preterm neonates and neurological development A randomized controlled trial" Indian Pediatrics, 2015, vol. 52, No. 11, pp. 951-955.
Chinese Office Action for Appl No. 201880077557.1 dated May 22, 2024, 8 pages.

* cited by examiner

*Primary Examiner* — Rosanne Kosson
(74) *Attorney, Agent, or Firm* — K&L Gates LLP

(57) ABSTRACT

A maternal composition wherein said maternal composition is specifically formulated for a woman who has given birth prematurely or who is at risk of giving birth prematurely.

1 Claim, No Drawings

MATERNAL SUPPLEMENT

CROSS REFERENCE TO RELATED APPLICATIONS

The present application is a continuation of U.S. patent application Ser. No. 16/768,829, filed on Jun. 1, 2020, which is a National Stage of International Application No. PCT/EP2018/082923, filed on Nov. 29, 2018, which claims priority to European Patent Application No. 17205002.3, filed on Dec. 1, 2017, the entire contents of which are being incorporated herein by reference.

FIELD OF THE INVENTION

The invention relates to a maternal composition wherein said maternal composition is specifically formulated for a woman who has given birth prematurely or who is at risk of giving birth prematurely. The invention further relates to the use of said maternal composition to optimize the breast milk quality of a woman who has given birth prematurely, to optimize the growth and development of an infant or child who was born prematurely, and/or to prevent infection, lung disease, bone fractures or blindness in an infant or a child who was born prematurely.

BACKGROUND

According to the World Health Organisation (WHO), each year around 15 million babies are born prematurely, that is to say born before 37 completed weeks of pregnancy. Infants and children who are born prematurely are at an increased risk of suffering from sub optimal growth and development, as well as a variety of health problems including infection, lung disease, and blindness.

No one factor is believed to be responsible for the sub-optimal growth and development and the increased risk of health problems seen in infants and children who were born prematurely, but nutrition is thought to play a vital role.

The gold standard in infant nutrition is breastmilk. Breastmilk, and when possible, breastfeeding, is recommended for infants born prematurely. In the early days, infants born prematurely need breastmilk to be supplemented or fortified. However, once they have reached a postmenstrual age of 40 weeks (actual age–weeks born prematurely=postmenstrual age), the nutritional needs of infants born prematurely are considered to be the same as term born infants and, breast milk alone is usually considered adequate as a source of nutrition.

The inventors have now surprisingly found that when a preterm infant or child's postmenstrual age matches that of a term born infant or child's age, the breastmilk produced by its mother may not be of the same quality of the breastmilk produced by a mother of a term horn infant. In particular the inventors have found that when a preterm infant or child's postmenstrual age matches that of a term born infant or child's age, the breastmilk produced by its mother may comprise a lower concentration of one or more nutrient e.g. selenium, zinc, tocopherol, retinal and/or nicotinic acid.

Given that the nutritional needs are thought to be the same for a term born infant and an infant of the same postmenstrual age who was born prematurely, there is a need to optimize the quality, for example to increase the concentration of one or more nutrient e.g. selenium, zinc, tocopherol, retinal and/or nicotinic acid, in the breastmilk of a mother who has given birth prematurely.

There is also a need to ensure that infants who have been born prematurely receive optimized nutrition that is the same or similar to that received by term born infants.

There is also a need to optimize the growth and development of an infant or child that was born prematurely and/or to prevent infection, lung disease and/or, blindness, or the risk or severity thereof e.g. by optimizing nutritional intake in said infant.

It is an objection of the present invention to address one or more of these identified needs.

SUMMARY OF THE INVENTION

The invention is set out in the claims and in the detailed description included herein. The inventors have devised a maternal composition wherein said maternal composition is specifically formulated for a woman who has given birth prematurely or who is at risk of giving birth prematurely.

The maternal composition may comprise one or more vitamin or mineral for example it may comprise one or more of selenium, zinc, tocopherol, retinal and nicotinic acid.

If the maternal composition comprises selenium it may be within a range of 20-400 mcg/day; if the maternal composition comprises zinc it may be within a range of 20-100 mg/day; if the maternal composition comprises tocopherol it may be within a range of 11 to 1000 mg/day; if the maternal composition comprises retinal it may be within a range of 500-7300 micrograms/day and, if the maternal composition comprises nicotinic acid it may be within a range of 14 to 900 mg/day.

The maternal composition may be specifically formulated for a women who is at risk of giving birth prematurely and/or for a woman who has given birth prematurely. It may be a pre-pregnancy and/or pregnancy and/or lactation supplement.

The maternal composition of the invention may be used to optimize the breast milk quality of a woman e.g. a woman who has given birth prematurely. The maternal composition may also be used to treat and/or prevent the production of breast milk of sub optimal quality in a woman e.g. a woman who has given birth prematurely. The maternal composition may also be used to optimize the growth and development of an infant or a child e.g. an infant or child who was born prematurely, and may be used to prevent and/or reduce the risk or severity of infection, bone fractures, lung disease and/or blindness in an infant or a child e.g. an infant or child who was born prematurely The maternal composition may be administered in combination with a maternal composition that has not been specifically formulated for a woman who has given birth prematurely.

DETAILED DESCRIPTION

In an aspect of the present invention there is provided a maternal composition wherein said maternal composition is specifically formulated for a woman who has given birth prematurely or who is at risk of giving birth prematurely.

A woman who has given birth prematurely may be considered to be any women who has given birth before 37 completed weeks of pregnancy.

A maternal composition may be considered to be specifically formulated for a woman who has given birth prematurely if said composition was specifically manufactured for, or is marketed for, women who have given birth prematurely and/or who are at risk of giving birth prematurely.

The number of completed weeks of pregnancy may be calculated by determining the time that has elapsed since the first day of a woman's last menstrual period. For the purpose of the calculation, it should be borne in mind that the first day of a woman's last menstrual period is considered day zero and not day one. Days 0-6 therefore correspond to "completed week zero" and, days 7-13 to "completed week one".

When the date of the last normal menstrual period is not available, the number of completed weeks of pregnancy may be based on the best clinical estimate.

A woman who is considered at risk of giving birth prematurely may be any woman who is evaluated by a doctor as being at risk of preterm birth, or who has one or more risk factor, regardless of whether said risk factor is modifiable or non-modifiable.

Non limiting examples of non-modifiable factors include: history of preterm birth, family history of preterm birth, low socioeconomic status, extremes in maternal age such as teenagers (15-19) and women >35, multiple gestation, uterine abnormalities, prior excisional cervical procedures, previous curettage and the use of assisted reproductive technologies.

Non limiting examples of modifiable factors include: extremely high or low maternal body mass index (BMI), smoking, substance abuse, short inter-pregnancy interval, short cervical length, periodontal disease, bacterial vaginosis, late or no prenatal care, poor pregnancy weight gain, and untreated antenatal depression.

The inventors have found that when a preterm infant or child's postmenstrual age matches that of a term born infant or child's age, the breastmilk produced by its mother may comprise a lower concentration of one or more protein, vitamin and/or mineral.

Accordingly, in an embodiment of the present invention the maternal composition comprises a protein, a vitamin, a mineral, or a combination of any of the foregoing.

Non-limiting examples of proteins include caseins, alpha-lactalbumin, and/or lactoferrin.

Non-limiting examples of vitamins and minerals include iron, vitamin B6, vitamin B9, vitamin B12, calcium, magnesium, phosphorus, iron, zinc, copper, iodine, selenium, vitamin A or retinal activity equivalent (RAE) e.g. beta carotene or a mix of carotenoids, Vitamin C, Vitamin B1, niacin, folic acid, biotin, tocopherol, selenium.

In particular the inventors have found that when a preterm infant or child's postmenstrual age matches that of a term born infant or child's age, the breastmilk produced by its mother may comprise a lower concentration of one or more of the following proteins and/or vitamins and/or minerals: caseins, alpha-lactalbumin, lactoferrin, copper, selenium, zinc, tocopherol, retinal, nicotinic acid, and/or nicotinuric acid.

Accordingly, in an embodiment of the present invention the maternal composition comprises casein, alpha-lactalbumin, lactoferrin, copper, selenium, zinc, tocopherol, retinal, nicotinic acid, nicotinuric acid or any combination of any of the foregoing.

The maternal intake of selenium, zinc, tocopherol, retinal, and nicotinic acid is known to effect their concentration in breastmilk. It may therefore be particularly beneficial if the maternal supplement comprises one or more of these nutrients.

Accordingly, in an even more specific embodiment of the invention, the maternal composition comprises selenium, zinc, tocopherol, retinal, nicotinic acid or any combination of any of the foregoing.

In addition to proteins and/or vitamin and/or minerals, the composition of the invention may also comprise ingredients commonly used in maternal supplements. Non-limiting examples of such ingredients include: probiotics, lipids, carbohydrates, pharmaceutically active agents and, conventional additives such as anti-oxidants, stabilizers, emulsifiers, acidulants, thickeners, buffers or agents for pH adjustment, chelating agents, colorants, excipients, flavor agents, osmotic agents, pharmaceutically acceptable carriers, preservatives, sugars, sweeteners, texturizers, emulsifiers, and water.

It may be particularly beneficial if the maternal compositions of the invention comprise lipids e.g. Long chain polyunsaturated fatty acids. Some of these compounds are believed to impact the risk of preterm birth.

It may also be particularly beneficial if the maternal compositions of the invention comprises probiotics, these may help nutrients pass through the gut. Combining vitamins with probiotics may thus enhance the absorption of the vitamins.

The term probiotic as used herein refers to live probiotic bacteria, non-replicating probiotic bacteria, dead probiotic bacteria, non-viable probiotic bacteria, fragments of probiotic bacteria such as DNA, metabolites of probiotic bacteria, cytoplasmic compounds of probiotic bacteria, cell wall materials of probiotic bacteria, culture supernatants of probiotic bacteria, and combinations of any of the foregoing.

The probiotic may be live probiotic bacteria, non-replicating probiotic bacteria, dead probiotic bacteria, non-viable probiotic bacteria, and any combination thereof.

In an embodiment the maternal composition of the invention comprises selenium and/or zinc and/or tocopherol and/or retinal and/or nicotinic acid and no other vitamins or minerals and/or other ingredients having a health effect/benefit. The composition may comprise excipients e.g. added for technical reasons.

Ingredients having a health effect as referred to herein, are ingredients that have been added to give a health benefit as opposed to being added for technical reasons e.g. to stabilize or give bulk to a composition.

In another embodiment the maternal composition of the invention contains only selenium and/or zinc and/or tocopherol and/or retinal and/or nicotinic acid. These ingredients may be encapsulated. A maternal composition comprising only selenium and/or zinc and/or tocopherol and/or retinal and/or nicotinic acid may be more economical to make and sell.

Any of the nutrients mentioned herein may be used in the maternal composition of the invention in any amount. Skilled artisans will be able to determine appropriate amounts depending on the desired dosage of a nutrient. Dosages may depend on the age, size and health status of the woman to whom they are administered, on her lifestyle, as well as on her genetic heritage. Dosages may be in line with the recommended daily intakes (RDA) developed by organisations such as the Food and Nutrition Board of the National Academy of Sciences.

A particularly useful dose of selenium may be in the range of 20-400, 25 to 250, 26 to 85 and/or, to 70 mcg/day.

The selenium may be comprised in the composition of the invention in any form suitable for ingestion by a pregnant woman or a woman tying to conceive. For example, selenium may be comprised in the maternal composition in the form of sodium selenite, sodium selenite and sodium hydrogen selenite or a mixture of any of the foregoing.

As it is evident to the skilled person, different forms of selenium may provide different amounts of selenium in the composition. It will be nonetheless routine work for the skilled person to calculate the amount of ingredient needed to provide the claimed amount e.g. dose of selenium, based on the specification of the specific ingredient.

A particularly useful dose of zinc may be in the range of 20-100, 5 to 40, 7 to 13 or, 9.5 to 12 mg/day.

The zinc may be comprised in the composition of the invention in any form suitable for ingestion by a pregnant woman or a woman trying to conceive. For example, zinc may be comprised in the maternal composition in the form of zinc acetate, zinc chloride, zinc citrate, zinc gluconate, zinc lactate, zinc oxide, zinc sulphate, zinc carbonate or, a mixture of any of the foregoing.

As it is evident to the skilled person, different forms of zinc may provide different amounts of zinc in the composition. It will be nonetheless routine work for the skilled person to calculate the amount of ingredient needed to provide the claimed amount e.g. dose of zinc, based on the specification of the specific ingredient.

A particularly useful dose of tocopherol may be in the range of 11 to 1000, 7.5 to 300 or, 11 to 19 mg/day.

The term tocopherol as used herein refers to any form of tocopherol or a mixture of different tocopherols for example the term may refer to alpha-tocopherol, gamma-tocopherol or a mix of alpha-tocopherol, and gamma-tocopherol.

The tocopherol may be comprised in the composition of the invention in any form suitable for ingestion by a pregnant woman or a woman trying to conceive. For example, gamma tocopherol and/or alpha tocopherol may be comprised in the maternal composition in the form of tocopherol concentrate mix, Vitamin E (L), tocopherols mixed pure, Vitamin E (D,L), di-alpha tocopherol, Vitamin E (DL-alpha tocopheryl acetate) and tocopherol rich extract or, a mixture of any of the foregoing.

As it is evident to the skilled person, different forms of tocopherol may provide different amounts of tocopherol in the composition. It will be nonetheless routine work for the skilled person to calculate the amount of ingredient needed to provide the claimed amount e.g. dose of tocopherol (gamma, alpha or a combination thereof), based on the specification of the specific ingredient.

A particularly useful dose of retinal (vitamin A) may be in the range of 500-7300, 600 to 3000, 770 to 1300 or, 800 to 850 micrograms/day.

The retinal may be comprised in the composition of the invention in any form suitable for ingestion by a pregnant woman or a woman trying to conceive. For example, retinal may be comprised in the maternal composition in the form of retinal, retinyl acetate and retinyl palmitate, β-carotene or, a mixture of any of the foregoing.

As it is evident to the skilled person, different forms of retinal may provide different amounts of retinal in the composition. It will be nonetheless routine work for the skilled person to calculate the amount of ingredient needed to provide the claimed amount e.g. dose of retinal, based on the specification of the specific ingredient.

A particularly useful dose of Niacin (vitamin B3) may be in the range of 14 to 900, 17 to 120 or, 18 to 35 mg/day.

The niacin may be comprised in the composition of the invention in any form suitable for ingestion by a pregnant woman or a woman trying to conceive. For example, niacin may be comprised in the maternal composition in the form of nicotinic acid, nicotinamide or mixtures thereof.

As it is evident to the skilled person, different forms of retinal may provide different amounts of niacin in the composition. It will be nonetheless routine work for the skilled person to calculate the amount of ingredient needed to provide the claimed amount e.g. dose of niacin, based on the specification of the specific ingredient.

In an embodiment of the present invention there is provided a maternal composition of the invention wherein, if said maternal composition comprises selenium it is within a range of 20-400 mcg/day; if said maternal composition comprises zinc it is within a range of 20-100 mg/day; if said composition comprises tocopherol it is within a range of 11 to 1000 mg/day; if said maternal composition comprises retinal it is within a range of 500-7300 micrograms/day and wherein if said maternal composition comprises nicotinic acid it is within a range of 14 to 900 mg/day.

Example dosage ranges for other non-limiting examples of ingredients that may be comprised in the maternal composition of the invention may be 100 to 2500 mg of calcium, 35 to 350 mg of magnesium, 70 to 3500 mg of phosphorus, 2.7 to 45 mg of iron, 0.1 to 10 mg of copper, 15 22 to 1,100 μg of iodine, 8.5 to 850 mg of Vitamin C, 0.14 to 14 mg of Vitamin B1, 60 to 1000 μg of folic acid, 3 to 300 μg of biotin.

The dosages defined in the present application refer to amounts per daily dose. Accordingly, the amount of nutrient in a composition may vary depending upon whether it is intended to be consumed once a day or more or less frequently.

The maternal composition of the present invention may be administered to a woman desiring to get pregnant, to a pregnant woman and/or to a lactating woman.

If the maternal composition of the invention is administered to a woman desiring to get pregnant, it may be administered for example during at least 1, 2, 3 or 4 months preceding the pregnancy or desired pregnancy.

If the maternal composition is to be administered to a pregnant woman, the composition may be administered for at least 4, least 8, at least 12, at least 16, at least 20, at least 24, at least 28, at least 36 weeks during pregnancy. As the nutritional requirements increase in the second and third trimester of pregnancy, it may be particularly beneficial if the maternal composition of the invention is administered throughout the second and/or third trimester of pregnancy.

Administering the maternal composition pre pregnancy and/or during pregnancy may enable a woman to build up a store of one or more nutrient e.g. selenium and/or zinc and/or tocopherol and/or retinal and/or nicotinic acid ready the body to use during lactation.

If the maternal composition of the invention is administered to a lactating woman, it may be administered for any part of the lactation period for example up to 2 years, up to 1 year, up to 9, 8, 7, 6, 5, 4, 3, 2, 1 months post birth.

In an embodiment of the present invention the maternal composition is administered to a woman desiring to get pregnant, to a pregnant woman and/or to a lactating woman.

The inventors have found that when a preterm infant or child's postmenstrual age matches that of a term born infant or child's age, the breastmilk produced by its mother may not be of the same quality (comprise the same nutrients in the same quantities) of the breastmilk of a mother of a term born infant. Accordingly, it may be particularly beneficial if the maternal composition of the invention is administered when the infant of a woman who has given birth prematurely reaches the postmenstrual age of 38 weeks and beyond for example 38 weeks to 48 weeks, weeks to 48 weeks.

Accordingly, in an embodiment of the invention the maternal composition is administered to a woman who has given birth prematurely when her infant or child has reached the postmenstrual age of 38 weeks and beyond for example 38 weeks to 48 weeks, 40 weeks to 48 weeks.

The term "postmenstrual age" as used herein refers to the actual age of an infant—weeks born prematurely (before 40 completed weeks of pregnancy) e.g. If an infant is born at 36 weeks (4 weeks prematurely), 8 weeks post birth said infant would have an actual age of 44 weeks and a postmenstrual age of 40 weeks.

As used herein, the term maternal composition refers to any composition that has been specifically manufactured for consumption by a pregnant woman, or a woman trying to conceive, or a composition that is specifically marketed at pregnant women or women trying to conceive.

The maternal composition of the invention may be any type of composition that is suitable for administration to a woman who has given birth prematurely or who is at risk of giving birth prematurely. It may for example be a food product, a functional food product, a drink, (beverage), a dairy product or dairy substitute product, a pharmaceutical formulation or a supplement.

The term "dairy products", as used herein, refers to food products produced from animals such as cows, goats, sheep, yaks, horses, camels, and other mammals. Examples of dairy products are low-fat milk (e.g. 0.1%, 0.5% or 1.5% fat), fat-free milk, milk powder, whole milk, whole milk products, butter, buttermilk, buttermilk products, skim milk, skim milk, lactose free products, high milk-fat products, condensed milk, crème fraiche, cheese, ice cream and confectionery products, probiotic drinks or probiotic yoghurt type drinks. A dairy substitute product may be a soya, almond, or vegetable based dairy substitute e.g. a milk or yoghurt substitute.

The term "pharmaceutical formulation" as used herein, refers to a composition comprising at least one pharmaceutically active agent, chemical substance or drug. The pharmaceutical formulation may be in solid or liquid form and can comprise at least one additional active agent, carrier, vehicle, excipient, or auxiliary agent identifiable by a person skilled in the art.

The pharmaceutically active agents may for example be an agent to prevent or minimize the risk of preterm birth. The pharmaceutical formulation can be in the form of a tablet, capsule, granules, powder, liquid or syrup.

The term "beverage product" as used herein, refers to a nutritional product in liquid or semi-liquid form that may be safely consumed by an individual.

The term "food product", as used herein, refers to any kind of product that may be safely consumed by a woman who has given birth prematurely or who is at risk of giving birth prematurely. Said food product may be in solid, semi-solid or liquid form and may comprise one or more nutrients, foods or nutritional supplements. For instance, the food product may additional comprise the following nutrients and micronutrients: a source of proteins, a source of lipids, a source of carbohydrates, vitamins and minerals. The composition may also contain anti-oxidants, stabilizers (when provided in solid form) or emulsifiers (when provided in liquid form).

The term "functional food product" as used herein, refers to a food product providing an additional health-promoting or disease-preventing function to the individual. Food products and functional food products include for example cereal-based products, yogurts or other milk-derived products and bars.

The term "supplement" as used herein, refers to a nutritional product that provides nutrients e.g. vitamins and/or minerals to an individual that may otherwise not be consumed in sufficient quantities by said individual. Supplements may for example be provided in the form of a pill, a tablet, a lozenger, a chewy capsule or tablet, a tablet or capsule, or a powder supplement that can for example be dissolved in water or milk, or simply sprinkled on food.

Supplements typically provide selected nutrients without providing a significant portion of the overall nutritional needs of a subject. Typically they do not represent more than 0.1%, 1%, 5%, 10% or 20% of the daily energy need of a subject. In the context of the present invention the subject would be a woman trying to get pregnant, a pregnant woman and/or a lactating woman who has given birth prematurely or who is at risk of giving birth prematurely.

In an embodiment of the present invention the maternal composition is specifically formulated for a women who is at risk of giving birth prematurely or who has given birth prematurely and is a pre-pregnancy and/or pregnancy supplement and/or lactation supplement.

In an embodiment of the present invention the maternal composition is specifically formulated for a women who is at risk of giving birth and is a pre-pregnancy supplement.

In another embodiment of the present invention the maternal composition is specifically formulated for a women who has given birth prematurely and may be a lactation supplement.

The term "pregnancy supplement" as used herein refers to a supplement that is specifically formulated for administration to a woman who is trying to conceive and/or to a woman who is pregnant, or marketed towards a woman who is trying to conceive and/or a woman who is pregnant.

The term "lactation supplement" as used herein refers to a supplement that is specifically formulated for administration to a woman who is lactating, or marketed toward a woman who is lactating.

Administration of the maternal composition of the invention to a woman e.g. a woman who has given birth prematurely or who is a risk of giving birth prematurely, may optimise the quality of her breastmilk by increasing the concentration of at least one nutrient. In particular, the administration of the maternal composition of the invention may increase the concentration of one or more of selenium, zinc, tocopherol, retinal and/or, nicotinic acid in the breastmilk of a woman e.g. a woman who has given birth prematurely or who is a risk of giving birth prematurely.

Accordingly in another aspect of the present invention there is provided the use of a maternal composition as disclosed herein to optimise the breast milk quality of a woman e.g. a woman who has given birth prematurely or who is a risk of giving birth prematurely.

The breast milk quality may be considered optimised if the concentration of one or more nutrient e.g. selenium, zinc, tocopherol, retinal or nicotinic acid, is increased.

It is well within the purview of the skilled person to determine if administration of a composition of the invention to a woman increases the concentration of one or more nutrient in her breastmilk. In particular, the skilled person can measure and then compare the concentration of one or more nutrient e.g. selenium, zinc, tocopherol, retinal or nicotinic acid, found in the breastmilk of a woman to whom a composition of the invention has been administered, with that of a woman to whom a composition of the invention has not been administer. The skilled person could also measure the difference in the concentration of a nutrient in breastmilk in a woman prior and subsequent to administration of a composition of the invention.

The amount of selenium, zinc, tocopherol, retinal or nicotinic acid found in breast milk can be measured by well known techniques. The amount of selenium and/or zinc may for example be measured using inductively coupled plasma mass spectrometry. The amount of retinal and/or, tocopherol acid may for example be measured using ultra high performance liquid chromatography with UV/Visible or fluorimetric detection. The amount of Nicotinic acid may for example be measured as set out in Redeuil et al, (2017) "A Novel Methodology for the Quantification of B-Vitamers in Breast Milk". J Anal Bioanal Tech 8: 352. doi: 10.4172/2155-9872.1000352.

In optimizing the concentration of one or more nutrient e.g. selenium, zinc, tocopherol, retinal or nicotinic acid, in breastmilk, a composition of the invention may be used to treat or prevent the production of breast milk of sub optimal quality in a woman e.g. a woman who has given birth prematurely or who is a risk of giving birth prematurely.

Breast milk quality may for example be considered sub-optimal if the concentration of one or more nutrient e.g. selenium, zinc, tocopherol, retinal or nicotinic acid is below the average value found in breastmilk produced by mothers who have given birth at term.

Accordingly, in another aspect of the present invention there is provided a maternal composition as disclosed herein for use in the treatment or prevention of the production of breast milk of sub optimal quality in a woman e.g. a woman who has given birth prematurely or who is a risk of giving birth prematurely.

In yet another aspect of the present invention there is provided the use of a maternal composition as disclosed herein in the manufacture of a composition for use in the treatment or prevention of the production of breast milk of sub optimal quality in a woman e.g. a woman who has given birth prematurely or who is a risk of giving birth prematurely.

The average value of selenium found in the breastmilk of a mother who has given birth at term is 1.55 mcg/100 ml The average value of zinc found in the breastmilk of a mother who has given birth at term is 355.4 mcg/100 ml.

The average value of retinal found in the breastmilk of a mother who has given birth at et is 106.4 mg/100 ml.

The average value of tocopherol found in the breastmilk of a mother who has given birth at term is 732.8 mg/100 ml.

The average value of alpha tocopherol found in the breastmilk of a mother who has given birth at term is 690.3 mg/100 ml.

The average value of gamma tocopherol found in the breastmilk of a mother who has given birth at term is 42.5 mg/100 ml.

The average value of nicotinic acid found in the breastmilk of a mother who has given birth at term is 3.53 mcg/100 ml.

Breastmilk quality and the amount of various nutrients an infant receives can impact numerous health parameters. Accordingly, it is important that a breastfeeding infant or child receives breastmilk of an optimised quality, and to try and treat and/or prevent women producing breastmilk of a sub-optimal quality.

Selenium, zinc, tocopherol, retinal or nicotinic acid are all necessary for optimal growth and development in an infant or child. Increasing their concentration in breastmilk may prevent sub-optimal growth and development (including growth stunting and/or developmental delays) and may promote optimal growth and development in an infant or child e.g. an infant or child who was born prematurely.

Accordingly, in another aspect of the present invention there is provided the use of a maternal composition as disclosed herein to optimise the growth and development of an infant or a child, in particular an infant or child who was born prematurely.

The term "optimise" as used herein includes improve or enhance.

The term "infant" will in the context of the present invention mean a human under the age of 12 months.

The term "child" as used herein refers to a human of 12 months to 12 years of age, for example 12 months to 5 years of age, 12 months to 4, 3, 2, years of age.

If an infant or child was born prematurely said infant or child was born before 37 completed weeks of pregnancy and may be referred to as a preterm infant or, an infant or child who was born prematurely.

In another aspect of the present invention there is provided the use of a maternal composition as disclosed herein in the treatment or prevention of sub-optimal growth and development, infection, lung disease, bone fractures and/or, blindness in an infant or child that was born prematurely.

The term "prevent" as used herein includes prevention and reducing the risk of a condition.

The term "prevent" as used herein includes treatment and reducing the severity of a condition.

In another aspect of the present invention there is provided the use of a maternal composition as disclosed herein in the manufacture of a composition for use in the treatment or prevention of sub-optimal growth, including growth stunting, and/or sub-optimal development including developmental delays, infection, lung disease, blindness and, bone fractures in an infant or child that was born prematurely.

In another aspect of the present invention there is provided a method of treating or preventing the production of breast milk of sub optimal quality in a woman e.g. a woman who has given birth prematurely or who is a risk of giving birth prematurely, said method comprising administering to said woman a maternal composition as disclosed herein.

In another aspect of the present invention there is provided a method of treating or preventing sub-optimal growth, including growth stunting, and/or sub-optimal development including developmental delays, infection, lung disease, blindness and, bone fractures in an infant or child that was born prematurely, said method comprising administering to said woman a maternal composition as disclosed herein.

It may be particularly beneficial if the composition of the invention is administered in combination with a maternal supplement that has not been specifically formulated for a woman who has given birth prematurely.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth. All references to singular characteristics or limitations of the present invention shall include the corresponding plural characteristic or limitation, and vice versa, unless otherwise specified or clearly implied to the contrary by the context in which the reference, is made.

The term "and/or" used in the context of the "X and/or Y" should be interpreted as "X", or "Y", or "X and V".

Unless defined otherwise, all technical and scientific terms used herein have the same meaning as commonly understood by one of ordinary skilled in the art.

The present invention will now be described in further details by the way of the following examples.

EXAMPLES

Example 1: Comparison of Breast Milk from Mothers Delivering Prematurely with Milk of Mothers Delivering at Term In the present study the content of breast milk of mothers delivering prematurely was compared in terms of several nutrients with the content of breast milk of mothers delivering at term. The comparison was performed over a period ranging from 38 to 48 weeks of babies' postmenstrual age.

Methods Used for Breast Milk Analysis

Minerals:

Copper (Cu), Selenium (Se) and Zinc (Zn) were analyzed according to the following method: 0.0.7 ml of breast milk were transferred into PFA vessels and mineralized in a GEM Microwave digestion system using Nitric acid ($HNO_3$)/Hydrogen peroxide ($H_2O_2$). Mineralized samples were transferred to PE tubes and diluted to 15 ml using Millipore water. Samples were then re-diluted after addition of Germanium (Ge) and Tellurium (Te) as internal standard and analyzed by Inductively Coupled Plasma Mass Spectrometry (ICP-MS, Nexion 300 D, Perkin Elmer). A Quality Control (QC) sample was included in the analysis.

Vitamins:

B-vitamins were analyzed according to reference Redeuil et al, (2017) "A Novel Methodology for the Quantification of B-Vitamers in Breast Milk". T Anal Bioanal Tech 8: 352. doi: 10.4172/2155-9872.1000352.

The analysis of vitamin A (carotenoids) and vitamin E (tocopherols) was performed according to the following method: vitamin E (a-tocopherol and y-tocopherol), provitamin A carotenoids (β-carotene and β-cryptoxanthin), as well as other carotenoids such as lycopene, lutein and zeaxanthin in human milk were extracted by ethanolic protein precipitation and liquid-liquid extraction with a mixture of n-hexane and ethyl acetate containing butylated hydroxytoluene (BHT). The extracts were then evaporated to dryness under a nitrogen stream. The dried extracts were re-dissolved in isooctane-ethyl acetate and analysis was performed by Ultra High Performance Liquid Chromatography with UV/Visible or fluorimetric detection (UHPLC-UV-FLD, Waters Acquity UPLC; Thermo Hypersil GOLD Silica column, 1.9 μm, 200×2.1 mm). Analytes were quantified by external calibration using authentic standards, rac-tocol (Matreya LLC, 1797; CAS No 119-98-2) and trans-β-apo-8'-carotenal (Sigma-Aldrich, 10810; CAS No 1107-26-2).

Sample Preparation: The milk sample or mixed standard solution (50 was transferred to a microtube (1.5-mL) and laminaritriose solution (0.5 mM, 50 μL) was added. After mixing, an aliquot (20 μL) was transferred to another microtube (1.5 ml) and 2AB labelling reagent 20 was added (2AB (0.35 M)+sodium cyanoborohydride (1 M) in DMSO/acetic acid (7/3), 200 μL). After mixing, the sample or standard was heated at 6S° C. for 2 h. The mixture was then cooled at 4° C. for 10 min prior to adding a water/acetonitrile mixture (25/75, 0.6 ml). Particles were removed by centrifugation (10000×g, 5 min) prior to transferring samples or standards to the LC system.

Liquid Chromatography: An Ultimate 3000-RS ultra-high performance liquid chromatography (UHPLC) system equipped with an RF-2000 fluorimeter (FLD) and a 2-way 10 port high pressure switching valve (all from Thermo Fisher Scientific, Waltham, USA). The columns were an Acquity BEH Glycan (1.7 μm, 2.1×150 mm) and VanGuard BEH amide (1.7 μm, 2.1×50 mm) both from Waters Corporation (Milford, USA). The guard column was installed between 30 injector and the 10-port valve. After injection, the sample was directed to the guard column with flow diverted to the waste to remove excess labelling reagents (0-2.3 min of gradient in table below), then the flow was directed through the analytical column and the oligosaccharides eluted using a gradient of ammonium formate (see table below). The flow rate was 0.5 ml min-1 and the analytical column was kept at 55° C. Detection was performed using a fluorimeter with excitation wavelength 330 nm and emission wavelength 420 nm.

| Time (min) | % Acetonitrile | % Ammonium Formate (50 mM) | Valve Position |
|---|---|---|---|
| 0 | 95 | 5 | Waste |
| 2.3 | 95 | 5 | Waste |
| 2.5 | 90 | 10 | Analysis |
| 4.9 | 90 | 10 | Analysis |
| 32.1 | 82 | 18 | Analysis |
| 48.1 | 80.5 | 19.5 | Analysis |
| 61.5 | 78.0 | 22.0 | Analysis |
| 89.0 | 74.6 | 25.4 | Analysis |
| 89.5 | 30 | 70 | Analysis |
| 92.0 | 30 | 70 | Analysis |
| 93.0 | 90 | 10 | Analysis |
| 98.0 | 90 | 10 | Analysis |
| 99.0 | 95 | 5 | Waste |
| 100 | 95 | 5 | Waste |

Proteins:

The individual proteins in human milk were analyzed using the LabChip system as described in Affolter M, et al. (2016) "Temporal Changes of Protein Composition in Breast Milk of Chinese Urban Mothers and Impact of Caesarean Section Delivery. Nutrients" 2016, 8, 504; doi:10.3390.

Statistical Analysis:

All statistical analyses were done with the statistical software R 3.2.3.

This particular analysis combines all observations across the lifespan of the trial (max 2 observations for preterm infants and max 8 for term infants).

A mixed linear model was used in comparing the two groups (PRE-TERM and TERM) in which the group and mode of delivery was considered as fixed effects. The within subject variability is taken into account by declaring the subjects as random effects. The main point of comparison is PRE-TERM vs TERM milk. The adjustment for mode of delivery is there because it is a confounding effect with term status given that there are higher proportion of preterm infants delivered by c-section.

Results

Significant different amounts of several proteins, vitamins, minerals and human milk oligosaccharides were measured in breast milk of mothers delivering prematurely when compared with term milk according to corresponding post menstrual age of 38 to 48 weeks.

Results obtained for such nutrients are reported in table 1.

For each nutrient, results reported in table 1 represent average values registered over weeks 38 to 48 postmenstrual age. Of note, only those nutrients where the difference between average value for term and preterm resulted to be statistically significant ($p<0.05$) have been included in the table.

In the light of the significant lower amount of the nutrients reported in table 1 in preterm milk, it results that a preterm infant that is exclusively breast fed receives, at the time of discharge from hospital (38 to 48 weeks), a significant lower amount of those nutrient as compared to a term infant of a corresponding post menstrual age who is exclusively breast-fed. As preterm infants already had a difficult start into life, optimal nutrition is of the upmost importance and the results obtained in this study demonstrate the need optimize the quality of breastmilk produced by mothers who have given birth prematurely in order to fill the gap in nutrients at discharge and to promote growth and good health in these premature infants.

TABLE 1

| NUTRIENT | Term | preterm | term-preterm | Units |
|---|---|---|---|---|
| Proteins | | | | |
| alpha-lactalbumin | 338.2 | 246.4 | 91.9 | mg/100 mL |
| caseins | 699.5 | 551.3 | 148.2 | mg/100 mL |
| lactoferrin | 328.3 | 255.7 | 72.5 | mg/100 mL |
| Minerals | | | | |
| Copper | 43.3 | 26.0 | 17.3 | µg/100 mL |
| Selenium | 1.55 | 1.22 | 0.33 | µg/100 mL |
| Zinc | 355.4 | 125.8 | 229.6 | µg/100 mL |
| Vitamins | | | | |
| alpha-tocopherol | 690.3 | 360.6 | 329.7 | µg/100 mL |
| gamma-tocopherol | 42.5 | 38.1 | 4.4 | µg/100 mL |
| total tocopherol | 732.8 | 398.7 | 334.1 | µg/100 mL |
| Vit A/retinol | 106.4 | 70.8 | 35.5 | µg/100 mL |
| nicotinic acid | 3.53 | 1.23 | 2.30 | µg/100 mL |

Example 2

An example of a maternal composition according to the present invention is given below in table 1:

TABLE 1

| Ingredient | Amount per daily dose |
|---|---|
| Zinc | 100 mg |
| tocopherol | 100 IU/ |
| nicotinic acid | 120 mg |
| Selenium | 200 µg |
| Retinol | 685-7218 µg |

The composition according to the present invention may be administered to a woman pre pregnancy, during pregnancy and/or during lactation.

The composition according to the present invention may be formulated with many variations without departing from the scope of the invention as defined in the claims.

All the embodiments as described in the above description shall be interpreted as illustrative and not in a limiting sense.

The invention claimed is:

1. A method of treating or reducing a risk and/or a severity of the production of breast milk of sub-optimal quality in a woman, said method comprising administering orally to said woman a therapeutically effective amount of a maternal composition comprising selenium, zinc, tocopherol, retinol, and nicotinic acid.

* * * * *